United States Patent
Winnett et al.

(10) Patent No.: US 8,545,516 B1
(45) Date of Patent: Oct. 1, 2013

(54) WATERPROOF MOTORIZED DEVICE HAVING ROTATING DERMABRASION APPARATUS TO PEEL CALLUSES AND HARDENED SKIN CELLS FROM LOCATIONS ON A PERSON'S FOOT

(76) Inventors: Harold G. Winnett, Los Angeles, CA (US); Steven L. Ober, Los Angeles, CA (US)

( * ) Notice: Subject to any disclaimer, the term of this patent is extended or adjusted under 35 U.S.C. 154(b) by 85 days.

(21) Appl. No.: 13/134,937

(22) Filed: Jun. 21, 2011

(51) Int. Cl.
*A61B 17/50* (2006.01)

(52) U.S. Cl.
USPC .......................................................... 606/131

(58) Field of Classification Search
USPC ...... 132/73.6, 76.4, 75.2; 451/163; 606/131; 15/88.2, 210.1
See application file for complete search history.

(56) References Cited

U.S. PATENT DOCUMENTS

| | | | |
|---|---|---|---|
| 4,061,136 A | 12/1977 | Vaniglia | |
| 5,345,640 A | 9/1994 | Goss | |
| 5,784,722 A | 7/1998 | Ureta et al. | |
| 5,913,313 A | 6/1999 | Brunderman | |
| 6,035,858 A * | 3/2000 | Park | 132/73 |
| 6,050,270 A * | 4/2000 | Tyshenko, Jr. | 132/73.6 |
| 6,142,156 A | 11/2000 | Brunderman | |
| 6,178,970 B1 * | 1/2001 | Purifoy et al. | 132/76.4 |
| 6,210,350 B1 | 4/2001 | Finch | |
| 6,523,546 B2 | 2/2003 | Jo et al. | |
| 6,684,444 B2 * | 2/2004 | Wheeler et al. | 15/110 |
| 6,708,351 B2 | 3/2004 | Sullinger | |
| 6,779,218 B1 | 8/2004 | Jusinski | |
| 6,848,451 B2 | 2/2005 | Postal et al. | |
| 7,267,125 B2 | 9/2007 | Nevakshonoff | |
| 7,270,641 B2 * | 9/2007 | Glucksman et al. | 601/112 |
| 7,278,431 B2 * | 10/2007 | Anderson et al. | 132/76.4 |
| 7,347,211 B1 | 3/2008 | Macklin | |
| 7,568,451 B2 | 8/2009 | Drelinger | |
| 7,578,300 B2 * | 8/2009 | Ryder | 132/73.6 |
| 7,581,545 B1 | 9/2009 | Moldawski et al. | |
| 7,712,474 B2 * | 5/2010 | Dixon | 132/76.4 |
| 8,162,956 B2 * | 4/2012 | Falk | 606/131 |
| 8,226,662 B2 * | 7/2012 | Song | 606/131 |
| 2004/0254587 A1 * | 12/2004 | Park | 606/131 |
| 2005/0103357 A1 | 5/2005 | Jo et al. | |
| 2009/0004953 A1 | 1/2009 | Kinsey | |
| 2009/0301507 A1 * | 12/2009 | Tes et al. | 132/73.6 |
| 2012/0023694 A1 * | 2/2012 | Nicas | 15/210.1 |

* cited by examiner

*Primary Examiner* — Ryan Severson
*Assistant Examiner* — Julie A Szpira
(74) *Attorney, Agent, or Firm* — Thomas I. Rozsa

(57) ABSTRACT

A device including a body having a bottom wall and a cover including a top wall and a sidewall which enclose an interior chamber so that the interior chamber is waterproof to enable the device to be placed in an enclosure where water comes in contact with the device, the interior chamber housing a mechanism by which a shaft or axle supporting a dermabrasion wheel is caused to rotate, the body further including an activation member which when activated causes the shaft and the dermabrasion wheel to rotate in either a counterclockwise direction or a clockwise direction, so that the dermabrasion wheel will peel hardened skin cells from a location on a foot when the location on the foot is placed against the dermabrasion wheel while the dermabrasion apparatus is rotating.

12 Claims, 6 Drawing Sheets

WATERPROOF MOTORIZED DEVICE HAVING ROTATING DERMABRASION APPARATUS TO PEEL CALLUSES AND HARDENED SKIN CELLS FROM LOCATIONS ON A PERSON'S FOOT

BACKGROUND OF THE INVENTION

1. Field of the Invention

The present invention relates to the field of pumice stones which are used to peel calluses from the back or from the underside of a person's toes. The present invention also relates to the field of motorized devices which are used to peel calluses in a more rapid and efficient way as opposed to a hand held pumice stone which is rubbed against the calluses by a back and forth motion from a user's hand.

2. Description of the Prior Art

The following 20 patents are relevant to the field of the present invention:

1. U.S. Pat. No. 4,061,136 issued to Giuseppe Vaniglia on Dec. 6, 1977 for "Portable Washer And Massager Apparatus For Bathtubs" (hereafter the "Vaniglia Patent");

2. U.S. Pat. No. 5,345,640 issued to Mary A. Goss on Sep. 13, 1994 for "Motorized Back Scrubber" (hereafter the "Goss Patent");

3. U.S. Pat. No. 5,784,722 issued to Luis A. Ureta et al. on Jul. 28, 1998 for "Shower Back Scrubber" (hereafter the "Ureta Patent");

4. U.S. Pat. No. 6,178,970 issued to Veena E. Purifoy et al. on Jan. 30, 2001 for "Foot Sander" (hereafter the "Purifoy Patent");

5. U.S. Pat. No. 6,210,350 issued to Mark K. Finch on Apr. 3, 2001 for "Device And Method For Removing In A Shower Or Bath Area Selected Skin Areas From A Bottom Foot Portion Of A Person" (hereafter the "Finch Patent");

6. U.S. Pat. No. 6,523,546 issued to Jeom-Sup Jo et al. on Feb. 25, 2003 for "Pedicure Sander Having Shock-Absorbing Unit" (hereafter the "Jo Patent");

7. U.S. Pat. No. 6,684,444 issued to Todd Wheeler et al. and assigned to Accurva, LLC on Feb. 3, 2004 for "Foot Scrubbing Device And Massaging Device" (hereafter the "Wheeler Patent");

8. U.S. Pat. No. 6,708,351 issued to Kelly Sullinger on Mar. 23, 2004 for "Dry Skin And Callus Removal Device" (hereafter the "Sullinger Patent");

9. U.S. Pat. No. 6,779,218 issued to Robert Jusinski on Aug. 24, 2004 for "Apparatus And Method For Ergonomic Basic Chiropody" (hereafter the "Jusinski Patent");

10. U.S. Pat. No. 6,848,451 issued to Robert T. Postal et al. and assigned to Twist2It, Inc. on Feb. 1, 2005 for "Drive Mechanism For Oscillatory Abrasion And Polishing Tool" (hereafter the "Postal Patent");

11. U.S. Pat. No. 7,278,431 issued to Paul M. Anderson et al. and assigned to Revlon Consumer Products Corporation on Oct. 9, 2007 for "Device for Smoothing Keratinous Surfaces" (hereafter the "Anderson Patent");

12. U.S. Pat. No. 7,347,211 issued to Elizabeth Macklin on Mar. 25, 2008 for "Electrically Operated Sander For Removing Calluses And Increasing Circulation" (hereafter the "Macklin Patent").

13. U.S. Pat. No. 5,913,313 issued to Pamela Jean Brunderman on Jun. 22, 1999 for "Footcare device And Method Of Using Same" (hereafter the "'313 Brunderman Patent");

14. U.S. Pat. No. 6,142,156 issued to Pamela Jean Brunderman on Nov. 7, 2000 for "Footcare device And Method Of Using Same" (hereafter the "'156 Brunderman Patent");

15. United States Published Patent Application No. 2005/0103357 to Jeom-Sup Jo et al. on May 19, 2005 for "Disposable Sand Cap For Removing Calluses And Callus Removal Device Having The Same" (hereafter the "Jo Published Patent Application");

16. U.S. Pat. No. 7,267,125 issued to Michael G. Nevakshonoff on Sep. 11, 2007 for "Device For Sanding Buffing or Grinding Elongate Objects" (hereafter the "Nevakshonoff Patent");

17. United States Published Patent Application No. 2009/0004953 to Verla M. Kinsey on Jan. 1, 2009 for "Skin Sander" (hereafter the "Kinsey Published Patent Application");

18. U.S. Pat. No. 7,568,451 issued to Jay Drelinger on Aug. 4, 2009 for "Rotary Nail Filing Apparatus For Animals" (hereafter the "Drelinger Patent");

19. U.S. Pat. No. 7,578,300 issued to Jeff G. Ryder on Aug. 25, 2009 for "Motorized Foot Sander" (hereafter the "Ryder Patent");

20. U.S. Pat. No. 7,581,545 issued to Clerice Moldawski et al. on Sep. 1, 2009 for "Dermabrasive Device" (hereafter the "Moldawski Patent").

The Vaniglia Patent is a portable power driven washer and massager apparatus for use in bathtubs. It includes a pair of roller brushes which are rotary driven by an electric motor, a heater and blower apparatus for directing hot air to the user, and means for readily mounting and dismounting the apparatus to a bathtub including adjustable locking means with suction cups. The device is intended to massage the back of a person.

The Goss Patent discloses a motorized scrubber for cleaning the back of a person. It has several rotating brushes and can be retained on the wall of a shower by suction cups. A soap dispenser provides soap to the center area of each of the brushes and another embodiment includes a water supply assembly for rinsing the user's back.

The Ureta Patent discloses a back scrubber for removable installation in a shower. A sponge is releasably held by a housing and has a thickness greater than the depths of the sidewall of the housing which retains it so that it can be used to sponge a person's back. The device discloses a back scrubber which is used to scrub a person's back and can be retained to the wall of a shower by suction cups and a sponge is used to scrub the person's back.

The Purifoy Patent discloses the concept of having a device for removing calluses from the underside of the foot by an orbital motion of a sander. It is a device that is held in the hand and is driven by a motor. A sheet of sandpaper or massaging pad is adopted to be removably attach to an orbital motion disc for foot sanding or massaging when applied thereto. The appliance body is orthopedically engineered to fit the palm of a user to enhance gripping. This is a device that is not intended to be used in a shower but is instead intended to be a personal grooming device to remove calluses from the back of the feet presumably when the person may be in the bathroom but not necessarily in a water environment such as a shower or bathtub.

The Finch Patent discloses a foot device that is retained on the bottom of a shower floor by suction cups and has a device which essentially is depicted in FIGS. 1 through 5 and is generally arch shaped and has abrasive material on it so that a person can rub each foot on the respective side of the abrasive material to remove calluses from the bottom of the feet. The device itself is stationary and the person has to move back and forth to remove the calluses from the bottom of the feet.

The Jo Patent discloses a handheld pedicure sander which is used to remove calluses from the bottom of the feet but it is not a device that is used in a shower or a water environment but instead is a handheld device. Specifically, referring to the patent text beginning on Column 3 Line 8, the patent states:

> "As shown in the drawings, the pedicure sander 1 of this invention has cylindrical rotary body 10, rotatably held by a bracket 50 at its drive shaft 32 and covered with a safety housing 16 at its top. In the present invention, the rotary body 10 may be preferably formed of a pumice stone or a float stone. However, it is more preferable to make the body 10 using a plastic material or metal. The drive shaft 32 is fixedly set along the central axis of the body 10.
>
> The rotary body 10 also has two axial fixing grooves 12 and 12a on its external surface such that the two grooves 12 and 12a are arranged in a line. Each of the two fixing grooves 12 and 12a firmly hold opposite ends of an associated one of two abrasive sheets 20 and 20a, thus allowing the two sheets 20 and 20a to closely and firmly cover desired parts of the external surface of the body 10 without being undesirably removed from the body 10.
>
> The rotary body 10 is a cylindrical body, stepped on its external surface at a predetermined portion to form two large diameter annular parts at opposite end portions and a small diameter part 26 defined between the two large diameter annular parts. Of the two large diameter annular parts, one has a large width, while the other has a small width. The two fixing grooves 12 and 12a are formed on the two large diameter annular parts, with the two abrasive sheets 20 and 20a covering the two large diameter annular parts to form a wide abrasive part 22 and a narrow abrasive part 22a."

The Wheeler Patent discloses a foot scrubbing and massaging device. The patent discloses a foot scrubber and massager formed of modular parts. The broadest claim is Claim 1 which reads as follows:

> "A foot scrubber comprising:
> a base module having an upper and a lower surface, wherein said base module is configured to cradle and substantially conform to a foot; and
> a customizable bristle module, said bristle module capable of being secured to said upper surface of said base module and said bristle module having a plurality of bristles extending outward from said bristle module, wherein said customizable bristle module may be customized to accommodate at least one plurality of interchangeable attachments."

The Sullinger Patent discloses a dry skin and callus removal device. The device for removing calluses and dry skin includes a base 2 with a rim 24 and a support 30 for a block of pumice 15. The base 2 has a keyhole 8 and the pumice block 15 has a receiving hole 16 to accommodate suction cups 20. Specifically, Claim 1 of the patent reads as follows:

> "A non-hand held device for the removal of dry skin and calluses from the human body comprising:
> (a) a planar base;
> (b) a block formed entirely of abrasive material supported by said base, said block of abrasive material having a planar lower surface and an upper surface, the entirety of which is concave, for abrasion; and
> (c) a plurality of suction cups attachable to said base."

The Jusinski Patent discloses an apparatus and method for ergonomic basic chiropody. It discloses a device which apparently needs to be positioned in a corner portion of the location so it is parallel to two perpendicular walls and the device operates to remove calluses from the feet.

The Postal Patent discloses a drive mechanism for oscillatory abrasion and polishing. It is a handheld tool which can be connected to a power source and which can be used for various abrading applications including manicuring, polishing and dermabrasion.

The Anderson Patent discloses a device for abrading the underside of a foot for removing calluses, corns, etc. The device has a concave and a convex surface so that the different locations of the foot can be massaged and calluses abraded away as illustrated in FIGS. 1 through 3. The claims require the device to be in a figure 8 configuration with a concave portion on one side and a convex portion on the other side.

The Macklin Patent discloses:

> "An electrically operated sander for removing calluses and increasing circulation, having a rectangular base unit for insertion into a docking unit. The base unit has a rear end, and includes a movable base plate having rounded edges and a grainy surface area and a gripping handle. The gripping handle extends outwardly from the base unit and defines a curved junction before extending horizontally toward the rear end of the base unit. The base unit houses a motor having a drive shaft mechanically linked to the base plate. A rotating two position on-off switch actuates the motor, causing the base plate to vibrate. A rectangular docking unit has a hollow cavity for accepting the gripping handle of the base unit therein for allowing users a hands free method of removing calluses."

The only independent claim of invention which is Claim 1 reads as follows:

> "A hands free method of removing calluses from hands or feet using an electrically operated sander, having a base unit having an on-off switch having an on position and an off position, a motor, a base plate having a grainy surface area, and having a docking unit, the steps comprising: positioning the base unit into the docking unit;
> vibrating the grainy surface of the base plate by actuating the on-off switch to the on position; and
> positioning calluses against the grainy surface and applying slight pressure while calluses are slowly removed."

The '313 Brunderman Patent contains essentially two solid objects which contain abrading material on it. There is a mound 34 on which you can rub the foot against and there is also a toe stick 32 with an abrasive surface 36 which fits within the mound so that it can be used to remove calluses from the toes.

The '156 Brunderman Patent issued in 2000 and is a continuation application of the previous Brunderman Patent.

In each of these Brunderman Patents, we are dealing with a solid object and are not dealing with anything providing rotary motion.

The Jo Published Patent Application discloses:

> "The present invention provides a disposable sand cap for removing calluses and a callus removal device having the same. The disposable sand cap for removing calluses includes a cap body which has a " "-shaped cross-section and is made of a synthetic resin, and an abrasive sand which has a 60.about.90 mesh particle size and is attached on a lower end surface of the cap body with a bonding agent. The callus removal device has the disposable sand cap with the abrasive sand. The callus removal device includes a grip part having an elliptical shape, with a plurality of finger grooves provided at several predetermined positions around a circumferential outer surface of the grip part, thus allowing fingers of a user to be placed on finger grooves. The callus removal device further includes a sand cap support part extending downwards from a lower portion of the grip part, with an insert ring provided around a circumferential outer surface of the sand cap support part. The callus removal device further includes an intermediate depression part provided between the grip part and the sand cap support part while being depressed inwards."

The Nevakshonoff Patent discloses a device for sanding and buffing objects which has a rotary device on top of an elongated shaft.

The Kinsey Published Patent Application discloses:

"A skin sander for removing dead skin such as calluses and rough dry skin, including a housing, electric motor, and an oscillating sanding surface. The skin sander is ergonomically designed for use by various sized hands with minimal effort."

The Drelinger Patent discloses:

"A rotary nail filing apparatus for animals is described that includes a shroud or housing, an opening in the shroud that is suitable sized and shaped to allow an end portion of an animal's nail to be put through the opening, and a suitably shaped and oriented rotary grinder that is contained within the shroud grinding at least a portion of an animal's nail when put through the opening, where at least a portion of the nail particles that are grinded away by the rotary grinder are contained in a portion of the shroud. In some embodiments, the rotary grinder position/orientation and/or its surface are adjustable and/or replaceable."

This patent discloses an object having a rotary motion for the purpose of sanding down an animal's nails.

The Ryder Patent discloses a hand sander where there is an abrasive method on the bottom of the device and it can be rubbed against the skin to abrade calluses, etc.

The Moldawski Patent discloses:

"A lightweight, portable, electrically-powered dermabrasive device adapted to gently and painlessly remove keratinized epidermal portions of the hands and feet. The dermabrasive device includes a protective shield which shields user against contact from flakes of flying or ejected epidermis or other detritus."

There is a significant need for an improved dermabrasion device to remove calluses which can be operated in a water environment such as a shower or bathtub and is operated so that a person does not need to use the person's hands to operate the pumice stone when removing calluses from the underside of a person's feet.

SUMMARY OF THE INVENTION

The present invention is a device including a body having a bottom wall and a cover including a top wall and a sidewall which enclose an interior chamber so that the interior chamber is waterproof to enable the device to be placed in an enclosure where water comes in contact with the device, the interior chamber housing a mechanism by which a shaft or axle supporting a dermabrasion wheel is caused to rotate, the body further comprising an activation member which when activated causes the shaft and the dermabrasion wheel to rotate in either a counterclockwise direction or a clockwise direction, so that the dermabrasion wheel will peel hardened skin cells from a location on a foot when the location on the foot is placed against the dermabrasion wheel while the dermabrasion apparatus is rotating.

The present invention is a waterproof motorized pumice stone described more broadly as a dermabrasion apparatus used to peel calluses from the a person's foot. The most common location from which calluses are removed are the underside of the foot at the location of the back of the heel and the underside of the foot below the toes. It is within the spirit and scope of the present invention to provide a device which can remove calluses from any location on a person's foot.

A key object of the present invention is to provide a device to remove calluses which is operated in a water environment. The device is operated while the person is in water so that the person's skin and calluses are softened by the water to facilitate the removal of calluses. The most common use is in a shower, however the present invention can also be used in a bathtub or spa, or other water environment while a person is taking shower or bath or soaking in hot water so that the skin and calluses on the person's foot are softened so that the removal of calluses is achieved more readily than an environment where the skin is dry and the calluses are hard. The device can be used while the shower head is spraying water onto the person or while the person is sitting in a bathtub or spa and after the calluses have been softened by the moisture so that callus removal is facilitated. The device can also be used in a dry environment.

It is another object of the present invention to provide a waterproof device which is operated in a hands free manner so that person does not have to hold the device while the device is being operated to remove calluses and other dead skin from a person's foot.

It is an additional object of the present invention to provide a device which enables calluses and other dead skin to be removed from a person's foot while a person is standing in a shower (or seated in the shower) or resting in a bathtub or hot tub so that the person can place the location of the person's foot where the calluses and dead skin are to be removed directly against the device.

It is a further object of the present invention to provide a waterproof device which has a rotating pumice stone which is balanced in the center of the device so that the device will not tip over as pressure form a foot is placed against the rotating pumice stone.

It is also an object of the present invention to provide a device which has a waterproof motorized enclosure which has a switch in the middle of the device and which can be activated by pressing on the switch with a person's foot. The device is normally off and a battery circuit is turned on when the switch is pressed and the circuit can be turned on and off by subsequent pressing action against the switch.

It is additionally an object of the present invention to provide a device having a rotatable shaft which contains a rotating pumice stone. When the activation switch is pressed or activated once, the pumice stone rotates in the counterclockwise direction or clockwise direction. When the switch activated again, the device is turned off.

It is a further object of the present invention to enable the device to be operated in a water environment so that when the pumice stone is rotating, foot can be placed on the pumice stone so that the back portion of the heel is polished and calluses, corns and hardened skin on the heel are removed. In addition, a person can place the back of their toes such as the underside of the ball of their big toe and underside of the front portion of their foot against the rotating pumice stone so that calluses, corns and other hardened skin can be removed.

It is additionally an object of the present invention for the device to have suction cups so that it can be affixed to the floor or a shower or bathtub so that the body of the apparatus will not move while it is being operated to remove calluses, etc. In this way, a person will not slip or fall while the pumice stones are rotating since the device itself will not move from its location where it is affixed to the floor by the suction cups.

It is also an object of the present invention to have warning means such as bright colors, a reflector, or other visible indicia on the device or molded into the device so that the device is visible and a person will not inadvertently step on the device or trip over the device and hurt themselves.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
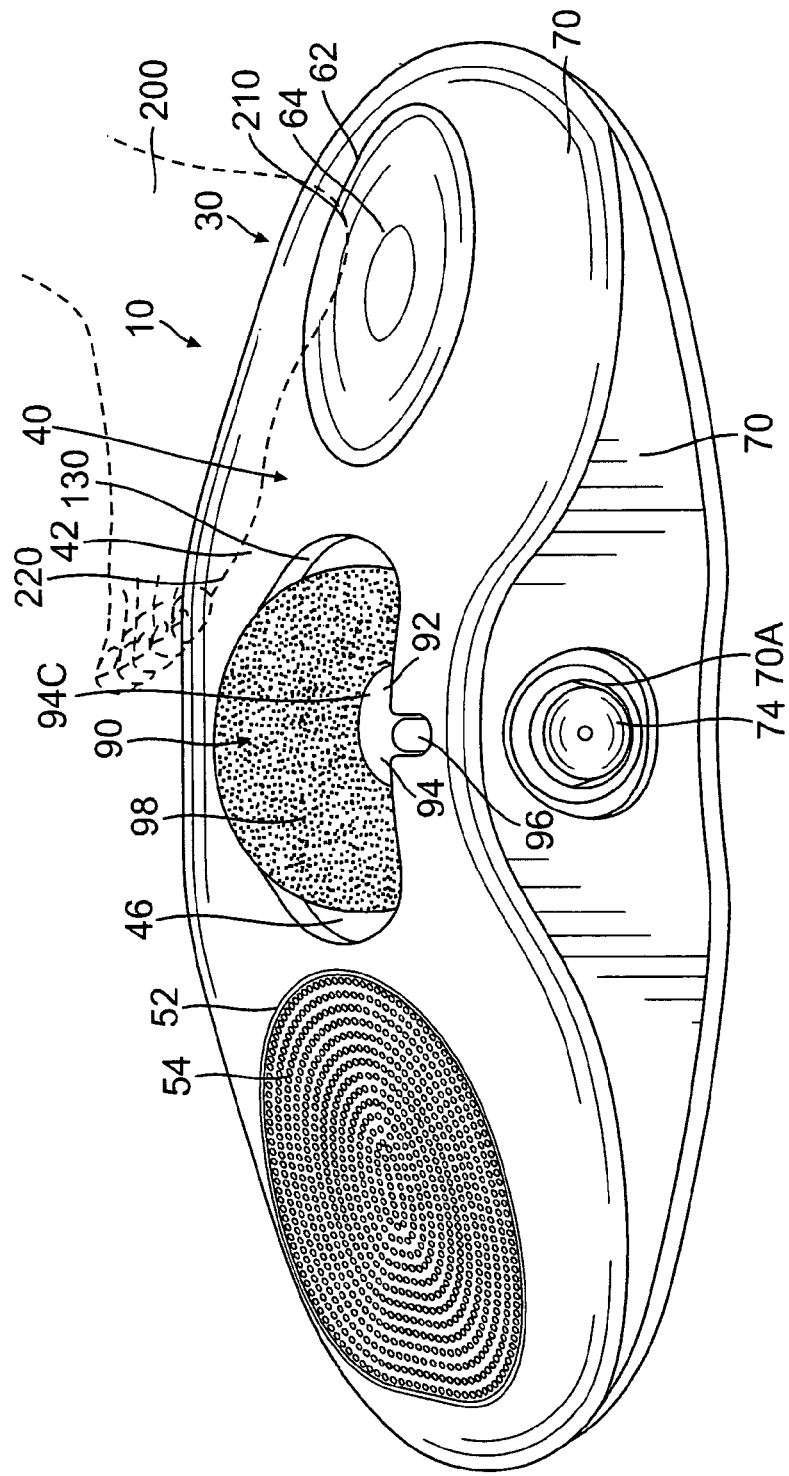
FIG. 1 is a perspective view of the present invention waterproof motorized device having a rotating dermabrasion apparatus, also illustrated in broken lines is a foot in a position to facilitate removal of dead skin cells from beneath toes.
Figure 2:
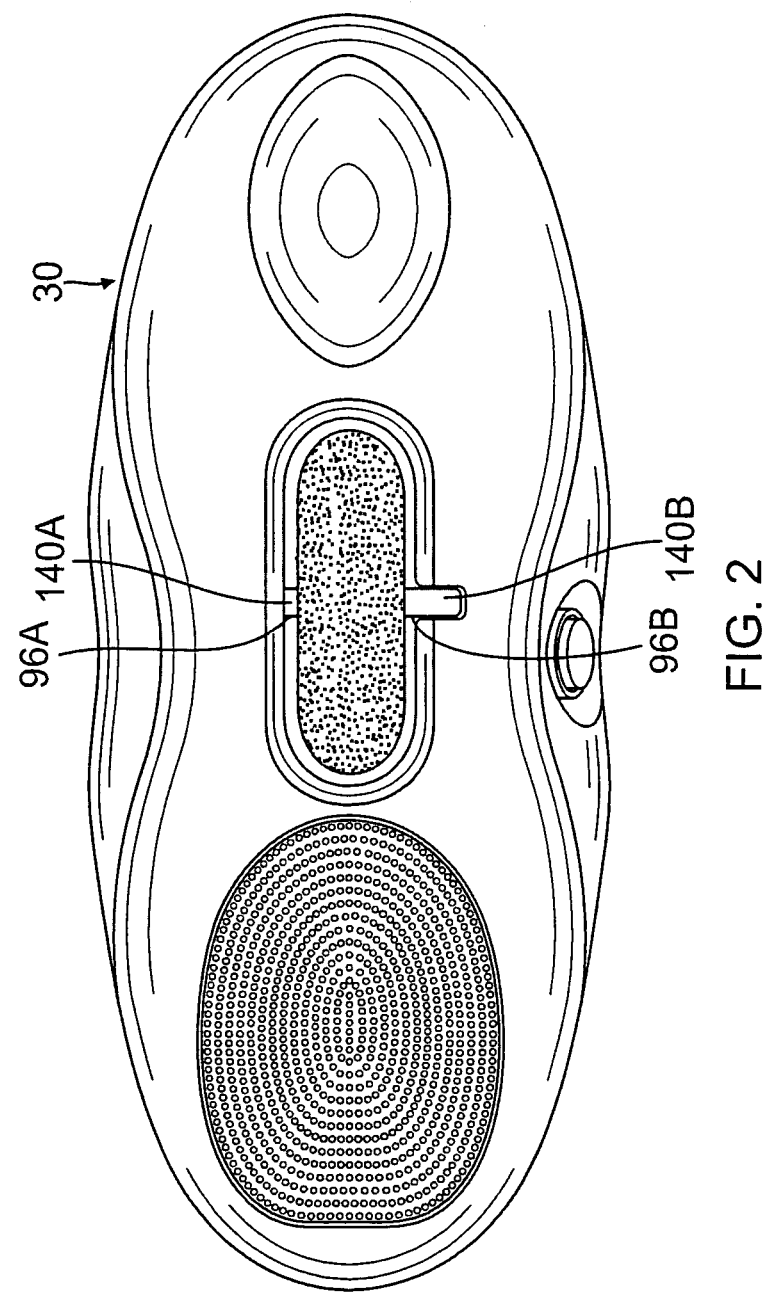
FIG. 2 is a top plan view of the present invention waterproof motorized device having a rotating dermabrasion apparatus, with a foot illustrated in broken lines.
Figure 3:
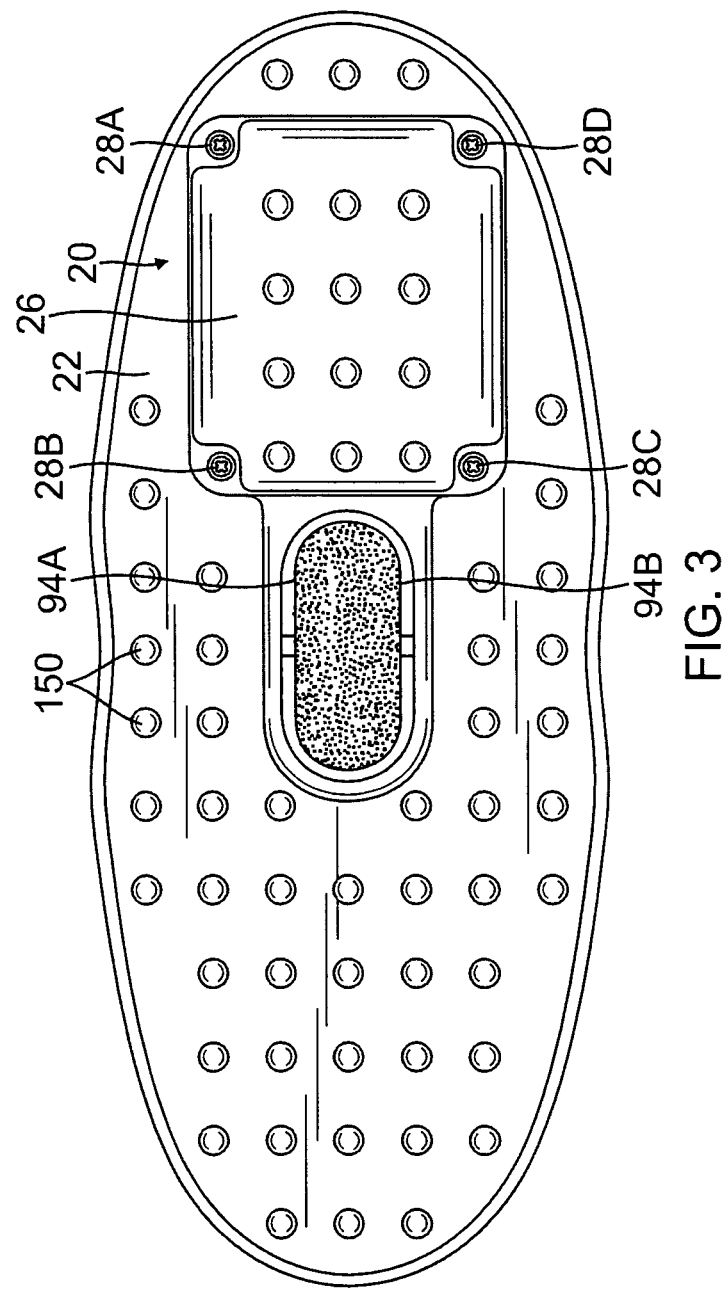
FIG. 3 is a bottom plan view of the present invention waterproof motorized rotating device having a rotating dermabrasion apparatus with suction cups affixed to the bottom of the device.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 6, there is illustrated a preferred embodiment of the present invention waterproof motorized rotating dermabrasion device 10 which comprises a bottom wall 20 having an exterior surface 22 and an interior surface 24. The bottom wall 20 is enclosed by a cover 30. The cover 30 has a top wall 40 with an exterior surface 42 and an interior surface 44 with a central opening 46 extending through the top wall 40. The exterior surface 42 and a pair of oppositely disposed depressions 52 and 62 respectively accommodate a resistance pad 54 and 64. The cover 30 includes a sidewall 70 which includes a side opening 72 to accommodate an on-off switch 74. The side opening 72 is shielded by a portion of sidewall 70A. The sidewall 70 has an exterior surface 76 and an interior surface 78. The cover 30 fits over the bottom wall 20 to create an interior chamber 80 surrounded by the interior surface 24 of bottom wall 20, the interior surface 44 of top wall 40 and the interior surface 78 of sidewall 70.

A key innovation of the present invention is a central rotating pumice stone 90 which is a wheel 92 having an interior body 94 supporting an axle 96 extending transversely from either transverse side 94A and 94B of the body 94, the exterior rim 94C of the body covered by abrasive material 98.

Figure 4:
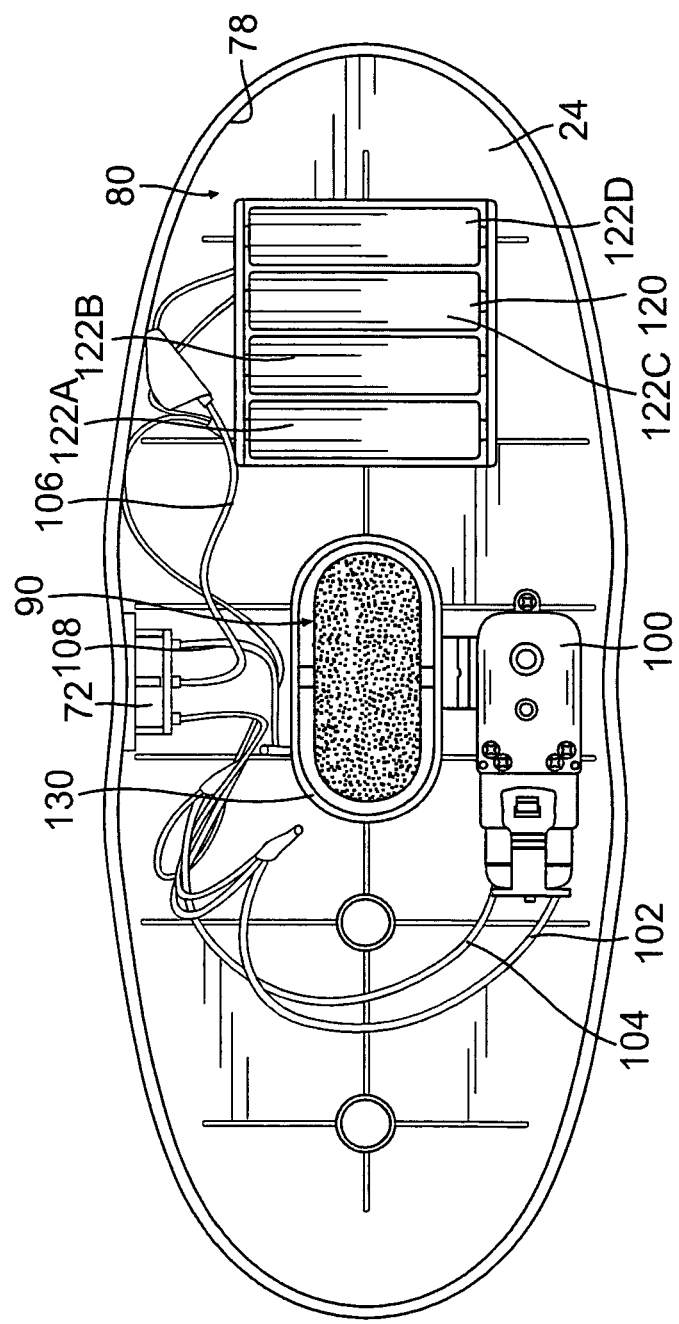
FIG. 4 is an interior view of the present invention waterproof motorized device having a rotating dermabrasion apparatus illustrating the electrical wiring of the device.

Referring to FIG. 4, the rotating pumice stone 90 is driven by a DC motor 100 which is connected to wires 102 and 104. Wire 102 is connected to a pole of the on-off switch 72 and wire 104 is connected to power pack 120 which can be a gang of batteries such as 4 AA batteries. Wire 106 connects the on-off switch 72 to the power pack 120 and wire 108 connects the on-off switch 72 to ground 110. Access door 26 is retained on bottom wall 20 by retaining means such as screws 28A, 28B, 28C and 28D. With the retaining means 28A, 28B, 28C and 28D removed, the access door 26 is opened to gain access to the power pack 120 to change batteries 122QA, 122 B, 122C and 122D. The interior chamber 80 is entirely sealed so that it is waterproof.

An interior shield 130 surrounds the opening 46 so that the interior chamber 80 is waterproof. The motor 100, wires 102, 104, 106 and 108 and power pack 120 are retained within chamber 80.

Figure 7:
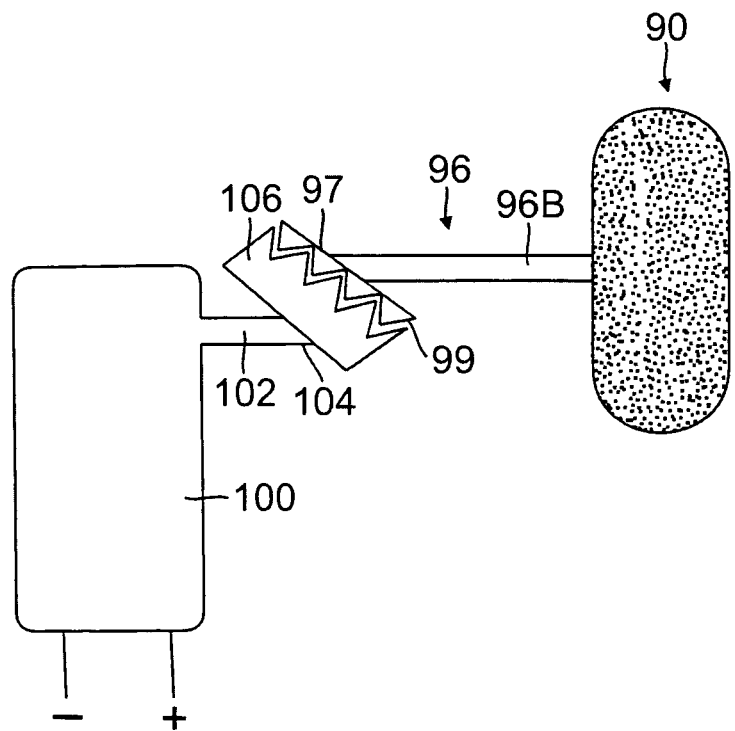
FIG. 7 is a perspective view showing the interconnection of the shaft from the motor and the shaft on which the pumice stone rotates.

Referring to FIG. 7, the motor 100 is connected to a shaft 102 which at the end 104 distal from the motor has an offset gear 106 formed to rotate in a given direction such as counter-clockwise. The axle 96 of the wheel 90 has a distal end 97 which is connected to an offset gear 99 which is formed to rotate in a direction opposite from the direction of the gear 106 on the motor shaft 102. The gear 99 can be formed to rotate in the clockwise direction. The gears 106 and 99 are intermeshed and when caused to rotate, because of the opposite orientation, the gears 106 and 99 remain together and will not separate.

The cover 30 has a central slot 140 extending into the shield 130 which surrounds the opening 46. The axle 96 has a short section 96A which extends transversely to face 94B of wheel body 94 and a long section 96B which extends transversely to face 94A of wheel body 94. The wheel 90 is retained within opening 46 of the cover, with the short section 96A of axle 96 retained in short slot section 140A while the long section 96B extends past slot section 140B to be engaged with the motor as illustrated in FIG. 7. The wheel 90 extends above the top surface 42 of cover 40 and when the switch 74 is moved or pushed to the "on" condition, the motor 100 causes its shaft 96 to rotate so that the intermeshed gears 99 and 106 cause the wheel 90 to rotate. The direction of rotation is either clockwise or counter-clockwise.

Movement retardation means such as suction cups 150 are placed on the exterior surface 22 of bottom wall 20 to help prevent the dermabrasion device from moving on the surface onto which it is placed.

Figure 5:
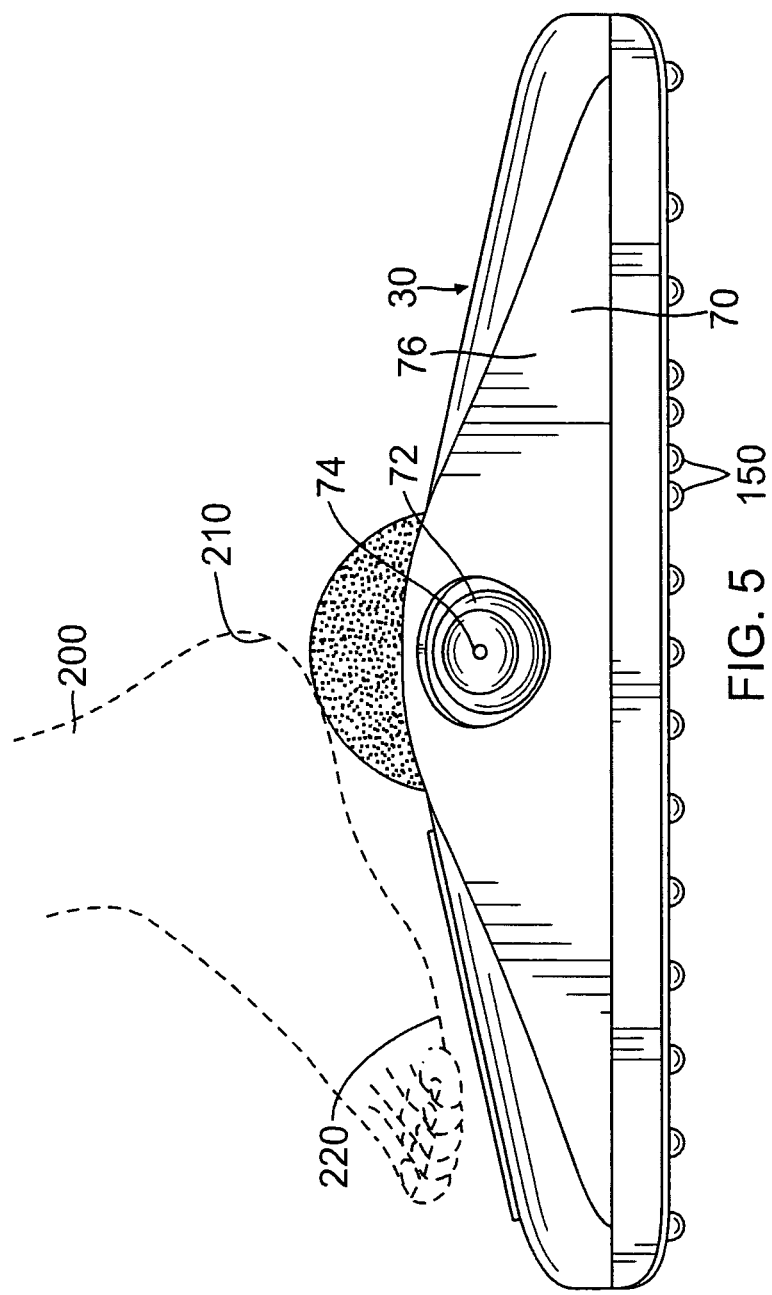
FIG. 5 is a side elevational view of the present invention waterproof motorized device having a rotating dermabrasion apparatus illustrating a foot shown in broken lines and positioned to enable the rotating pumice stone to be used to remove calluses, corns, and hardened skin from location below a person's heel.
Figure 6:
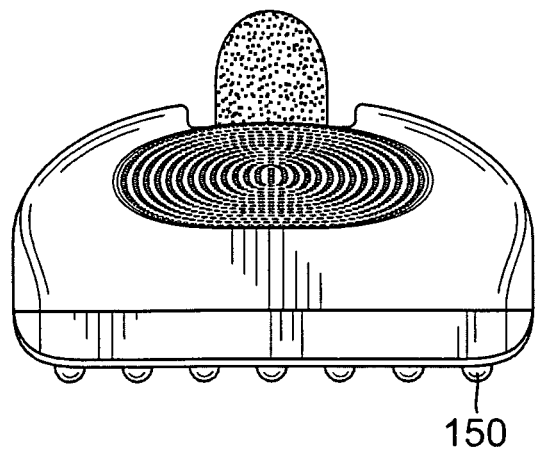
FIG. 6 is a front view of the present invention waterproof motorized device having a rotating dermabrasion apparatuses.

The dermabrasion device 10 is placed on a surface such a bathroom floor or a shower floor. As illustrated in FIG. 1 with a foot 200 illustrated in broken lines, a person places his/her 210 heel of a foot 200 onto a resistance pad 54 or 64 so that a portion 220 of the foot from which calluses or other dead skin is to be removed are aligned with the wheel 90 and with the abrasive material 98 of the wheel. When the switch 74 is activated, the wheel 98 rotates and the abrasive material rotates. The portion of the foot 220 placed against the abrasive material has calluses, dead skin cells, etc. removed by the rotating action of the wheel 96 and the abrasive material 98 peeling off the calluses and other dead skin. To remove calluses and other dead skin from other portions of the same foot or the opposite foot, the heel can be placed in the same resistance pad 54 or the opposite resistance pad 64 so that the proper area of the foot is aligned with the abrasive material 98 on wheel 96. The dermabrasion device 10 can be rotated 180 degrees if necessary for proper alignment of the specific area of the foot to be treated. As illustrated in FIG. 5, the foot portion 220 can be placed on a resistance pad 54 and the heel 210 can be placed against the dermabrasion wheel 98 to remove dead skin cells from that location of the foot.

The present invention wheel 96 is in the center of the dermabrasion device 10 so that it is properly balanced and will not tilt to one side as pressure from a foot is applied against the wheel 96. The waterproof enclosure enables the dermabrasion device 10 to be used in a shower while it is running. The movement retardation means 150 assists in preventing the device 10 from moving while in operation.

As an additional safety measure, warning means 170 such as florescent or other light reflecting material can be on the top surface 42 of cover 40 so that the device 10 is more visible to avoid a person accidentally tripping over the device 10, either in the bathroom or in a shower.

The fact that at least a portion of the axle 94A is within the shield 130 and the addition of the nature of the intermeshing gears 99 and 106 prevents the wheel 96 from flying out of the device 10 while it is in operation.

It will be appreciated that the device 10 can be used to remove dead skin cells from any location of the body but it is primary desired to remove dead skin cells from hard-to-reach locations on the foot. The device 10 is waterproof so it can be run while the source of water from a shower is running or after the source of water is turned off.

The motor 100 is preferably a battery operated DC motor.

The device 10 and its walls are preferably made of molded plastic but may be made of any rustproof and waterproof material.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A dermabrasion apparatus comprising:
  a. a bottom wall having an exterior surface and an interior surface, a cover having a top wall with an exterior surface and an interior surface with a central opening extending through the top wall from the exterior surface to the interior surface, the top surface of the cover having a pair of oppositely disposed depressions which respectively accommodate a resistance pad, the depressions respectively spaced apart from opposite ends of the central opening, the cover including a sidewall which includes a side opening to accommodate an on-off switch, the sidewall having an exterior surface and an interior surface, the cover fitting over the bottom wall to create an interior chamber surrounded by the interior surface of the bottom wall, the interior surface of the top wall and the interior surface of the sidewall;
  b. a central rotating pumice stone which is a wheel having an interior body supporting an axle extending transversely from opposite transverse sides of the body, an exterior rim of the body covered by abrasive material;
  c. the rotating pumice stone driven by a DC motor located within the interior chamber and which is electrically connected to a source of power located within the interior chamber, the DC motor and the source of power electrically connected to the on-off switch;
  d. an interior shield surrounding the central opening in the cover so that the interior chamber is waterproof;
  e. the DC motor connected to a shaft which at its end distal from the DC motor has an offset gear formed to rotate in a given direction, the axle of the wheel having an elongated section which at its distal end has an offset gear which is formed to rotate in a direction opposite from the direction of the offset gear on the DC motor shaft;
  f. the cover having a central slot extending into the shield which surrounds the central opening, the axle having a short section which extends transversely to a face of the wheel body and a long section which extends transversely to the face of the wheel body, the wheel partially retained within the central opening of the cover with the short section of the axle retained in a short slot section while the long section of the axle extends past a slot section so that its offset gear is intermeshed with the offset gear on the shaft of the DC motor, the wheel partially extending above the top surface of cover and when the on-off switch is in the "on" condition, the DC motor causes its shaft to rotate so that the intermeshed gears of the DC motor and axle cause the wheel to rotate so that the abrasive surface on the wheel facilitates dermabrasion of dead skin cells and calluses on a foot placed against the abrasive surface of the wheel, the wheel located at a central location of the apparatus to provide balance from external forces of a foot pushed against the wheel, the offset opposite orientation of the gears preventing the rotating wheel from flying out of the apparatus; and
  g. movement retardation means on the exterior surface of the bottom wall to help prevent the dermabrasion device from moving on a surface onto which it is placed so that the dermabrasion machine including the rotating pumice stone is operated hands free without requiring the dermabrasion machine to be held in a hand.

2. The dermabrasion apparatus in accordance with claim 1 further comprising warning means on the top surface of the cover so that the dermabrasion apparatus is visible in a darkened area.

3. The dermabrasion apparatus in accordance with claim 1 further comprising the bottom wall having an access door on its lower surface to facilitate gaining access to the source of power.

4. The dermabrasion apparatus in accordance with claim 1 further comprising the source of power is at least one battery.

5. A dermabrasion apparatus comprising:
  a. a bottom wall having an exterior surface and an interior surface, a cover having a top wall with an exterior surface and an interior surface with a central opening extending through the top wall from the exterior surface to the interior surface, the top surface of the cover having at least one depression which accommodates a resistance pad, the at least one depression spaced apart from an end of the central opening, the cover including a sidewall having an exterior surface and an interior surface, the cover fitting over the bottom wall to create an interior chamber surrounded by the interior surface of the bottom wall, the interior surface of the top wall and the interior surface of the sidewall;

b. a central rotating pumice stone which is a wheel having an interior body supporting an axle extending transversely from opposite transverse sides of the body, an exterior rim of the body covered by abrasive material;

c. the rotating pumice stone driven by a motor located within the interior chamber and which is electrically connected to a source of power located within the interior chamber, the motor and the source of power electrically connected to an on-off switch which is accessible from an exterior surface of a wall of the apparatus;

d. an interior shield surrounding the central opening in the cover so that the interior chamber is waterproof;

e. the motor connected to a shaft which at its end distal from the motor has a first engaging means, the axle of the wheel having an elongated section which at its distal end has a second engaging means;

f. the cover having a central slot extending into the shield which surrounds the central opening, the axle having a short section which extends transversely to a face of the wheel body and a long section which extends transversely to the face of the wheel body, the wheel partially retained within the central opening of the cover with the short section of the axle retained in a short slot section while the long section of the axle extends past a slot section so that its second engaging means is connected to the first engaging means on the shaft of the motor, the wheel partially extending above the top surface of cover and when the on-off switch is in the "on" condition, the motor causes its shaft to rotate so that the connected engaging means of the motor and axle cause the wheel to rotate so that the abrasive surface on the wheel facilitates dermabrasion of dead skin cells and calluses on a foot placed against the abrasive surface of the wheel, the wheel located at a central location of the apparatus to provide balance from external forces of a foot pushed against the wheel; and g. movement retardation means on the exterior surface of the bottom wall to help prevent the dermabrasion device from moving on a surface onto which it is placed so that the dermabrasion machine including the rotating pumice stone is operated hands free without requiring the dermabrasion machine to be held in a hand.

6. The dermabrasion apparatus in accordance with claim 5 further comprising warning means on the top surface of the cover so that the dermabrasion apparatus is visible in a darkened area.

7. The dermabrasion apparatus in accordance with claim 5 further comprising the bottom wall having an access door on its lower surface to facilitate gaining access to the source of power.

8. The dermabrasion apparatus in accordance with claim 5 further comprising the source of power is at least one battery.

9. A dermabrasion apparatus comprising:

a. a bottom wall having an exterior surface and an interior surface, a cover having a top wall with an exterior surface and an interior surface with a central opening extending through the top wall from the exterior surface to the interior surface, a sidewall having an exterior surface and an interior surface, the cover fitting over the bottom wall to create an interior chamber surrounded by the interior surface of the bottom wall, the interior surface of the top wall and the interior surface of the sidewall;

b. a central rotating pumice stone which is a wheel having an interior body supporting an axle extending transversely from opposite transverse sides of the body, an exterior rim of the body covered by abrasive material;

c. the rotating pumice stone driven by a motor located within the interior chamber and which is electrically connected to a source of power located within the interior chamber, the motor and the source of power electrically connected to an on-off switch which is accessible from an exterior surface of a wall of the apparatus;

d. shield means adjacent the central opening in the cover so that the interior chamber is waterproof;

e. the motor connected to a shaft which at its end distal from the motor has a first engaging means, the axle of the wheel having an elongated section which at its distal end has a second engaging means;

f. the cover having means to receive a short section of the axle which extends transversely to a face of the wheel body, the wheel partially retained within the central opening of the cover with the long section of the axle having its second engaging means connected to the first engaging means on the shaft of the motor, the wheel partially extending above the top surface of cover and when the on-off switch is in the "on" condition, the motor causes its shaft to rotate so that the connected engaging means of the motor and axle cause the wheel to rotate so that the abrasive surface on the wheel facilitates dermabrasion of a body part placed against the abrasive surface of the wheel, the wheel located at a central location of the apparatus to provide balance from external forces of a foot pushed against the wheel; and g. movement retardation means on the exterior surface of the bottom wall to help prevent the dermabrasion device from moving on a surface onto which it is placed so that the dermabrasion machine including the rotating pumice stone is operated hands free without requiring the dermabrasion machine to be held in a hand.

10. The dermabrasion apparatus in accordance with claim 9 further comprising warning means on the top surface of the cover so that the dermabrasion apparatus is visible in a darkened area.

11. The dermabrasion apparatus in accordance with claim 9 further comprising the bottom wall having an access door on its lower surface to facilitate gaining access to the source of power.

12. The dermabrasion apparatus in accordance with claim 9 further comprising the source of power is at least one battery.

* * * * *